United States Patent [19]
Anthony

[11] Patent Number: 5,293,555
[45] Date of Patent: Mar. 8, 1994

[54] SYSTEM AND METHOD FOR LOCATING MATERIAL FATIGUE USING MULTIPLE SENSORS

[75] Inventor: Michael Anthony, Santa Ana, Calif.

[73] Assignee: Hughes Aircraft Company, Los Angeles, Calif.

[21] Appl. No.: 705,247

[22] Filed: May 24, 1991

[51] Int. Cl.⁵ .................. G01S 3/80; G01N 29/14
[52] U.S. Cl. ..................... 364/508; 73/577; 73/583; 73/587
[58] Field of Search ........... 364/507, 508, 559, 551.01; 73/577, 583, 587

[56] References Cited

U.S. PATENT DOCUMENTS

| | | | |
|---|---|---|---|
| 4,470,122 | 9/1984 | Sarr | 73/621 |
| 4,531,411 | 7/1985 | Collins et al. | 73/587 |
| 4,535,629 | 8/1985 | Prine | 364/508 |
| 4,592,034 | 5/1986 | Sachse et al. | 73/587 |

*Primary Examiner*—Thomas G. Black
*Assistant Examiner*—Michael Zanelli
*Attorney, Agent, or Firm*—L. A. Alkov; W. K. Denson-Low

[57] ABSTRACT

A system for locating a fatigue point on a structure (10) employing a smart sensor patch (12) having three triangularly adjacent acoustic sensors (40 a,b,c). The smart sensor patch (12) has a local processor (34) associated therewith, which triangulates the location of the fatigue point.

15 Claims, 3 Drawing Sheets

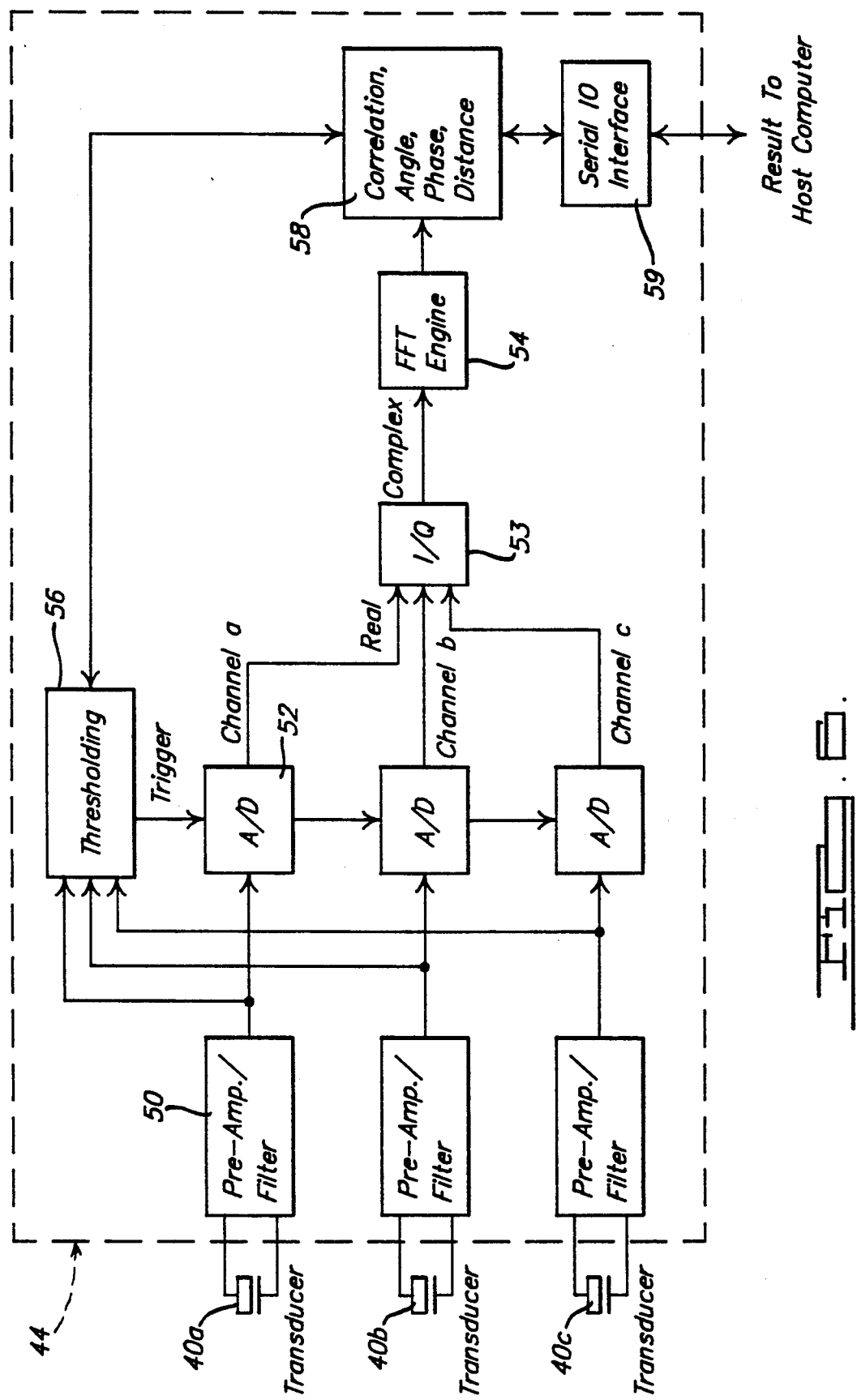

SYSTEM AND METHOD FOR LOCATING MATERIAL FATIGUE USING MULTIPLE SENSORS

BACKGROUND OF THE INVENTION

1. Technical Field

This invention relates to a system and method for determining the distance and direction of an acoustic emission, and more particularly to a system and method for locating fatigue points which minimizes the number of sensors needed to locate a fatigue point on a structure.

2. Discussion

Once a structural device, such as an airplane or a bridge, is put into service, it becomes necessary to detect and pinpoint fatigue points on the structure as they occur in order that they can be repaired. Because visual inspection can be both time consuming as well as inaccurate, acoustic sensors have been employed to detect fatigue points as they occur on the structure. One known application involves deploying a multitude of sensors over the surface of the structure. When a fatigue point occurs, the acoustic wave generated by the fatigue point is sensed by the acoustic sensors. Using the technique of geometric triangulation, the location of the fatigue point can be determined. One disadvantage, however, with this application is that each individual sensor has only a limited area of coverage. Therefore, a great number of individual sensors is required to cover large areas such as an aircraft skin. In this prior system, each sensor operates independently and the task of interpretating the sensor data and triangulating to determine the location of the fatigue point is processed at a central, or host, computer. Thus, a second disadvantage lies in the fact that as the size of the surface area desired to be monitored increases, the number of independent acoustic sensors increase, which results in increased complexity in both the wiring and the triangulation task of the central computer.

SUMMARY OF THE INVENTION

Pursuant to the present invention, a smart sensor array is employed to locate material fatigue points on a structure while minimizing the complexity of wiring and computational tasks. The smart array includes a sensor patch having three triangularly adjacent acoustic sensors. The sensor patch is electronically coupled to a local processor, where the location of the fatigue point is determined by triangulating the signals received at each of the three sensors of the sensor patch.

BRIEF DESCRIPTION OF THE DRAWINGS

The Various advantages of the present invention will become apparent to those skilled in the art after studying the following specification and by reference to the drawings in which:

FIG. 6 is a functional block diagram of the sensor patch and localized processing.

DESCRIPTION OF THE PREFERRED EMBODIMENT

Figure 1:
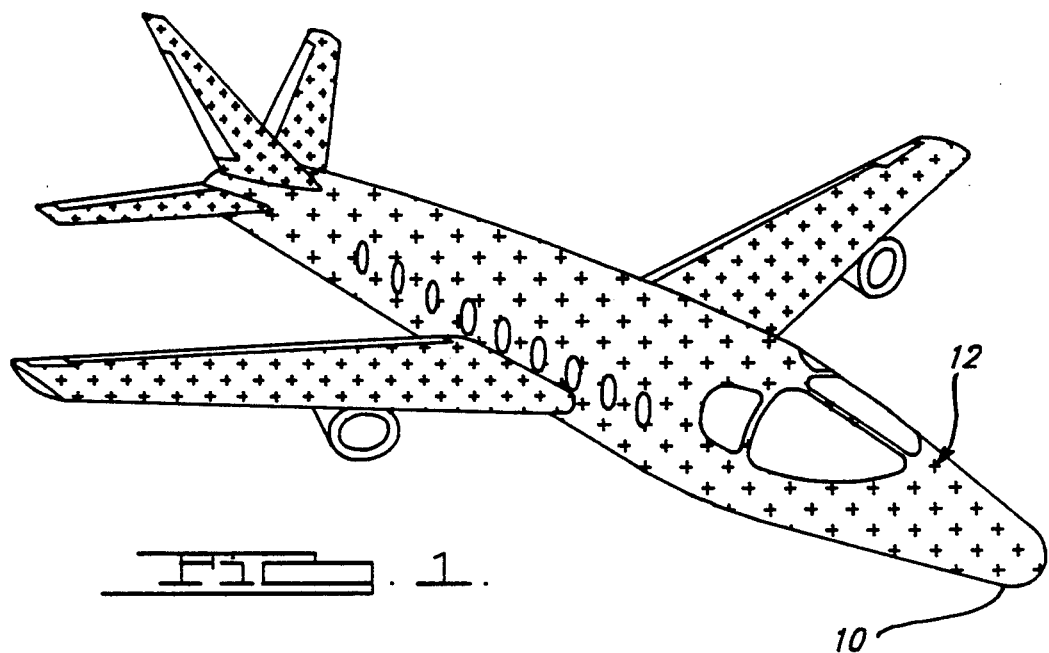
FIG. 1 is a diagram demonstrating one application of the smart array made in accordance with the teachings of the preferred embodiment of this invention.

FIG. 1 illustrates the present invention in use on an airplane structure. On the interior, or inner side, of the airplane's skin 10, a plurality of smart sensor patches 12 are affixed. The smart sensor patches 12 themselves are composed of a flexible material, allowing them to conform to the surface of the skin 10. The patches are affixed to the skin using an adhesive. The number of smart sensor patches 12 necessary to ensure that if a fatigue point occurs it will be detected is governed by the size of the surface area desired to be monitored, and, in general, the coverage radius of each smart sensor patch.

Figure 2:
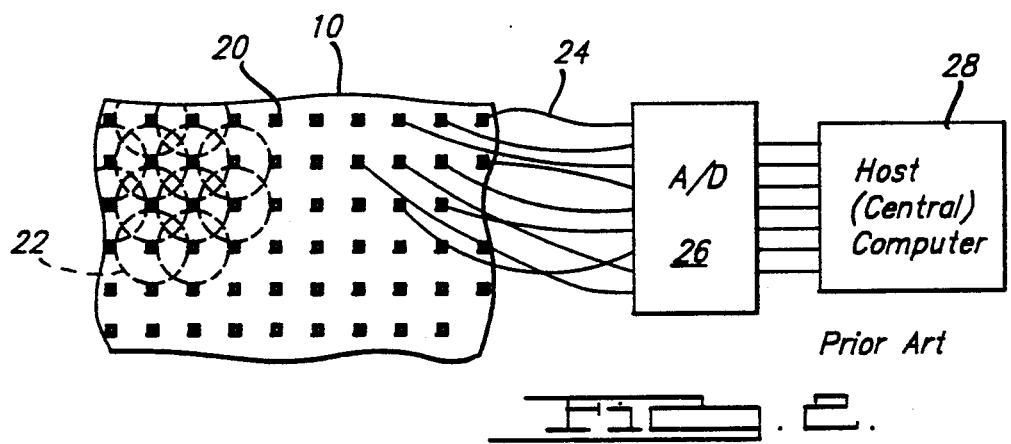
FIG. 2 is a diagram depicting the features and disadvantages of the PRIOR ART.

FIG. 2 is a diagram showing the prior art. In this particular example, the deployment of individual acoustic sensors 20 over the interior surface of an airplane wing skin 10 is shown. As can be seen, because each sensor 20 has a limited coverage area, generally described by coverage circles 22, a large number of these sensors 20 must be deployed across the interior surface of the skin 10 in order ensure that any fatigue point that occurs will be within the coverage circle 22 of at least three sensors 20 in order to ensure that the location of the fatigue point can be determined through triangulation. Furthermore, each sensor 20 is electronically linked 24 to a central signal sampling and conditioning device 26, such as an A/D converter. Once the signals from each individual sensor 20 are sampled, the signals are fed into a central processor 28 which performs the task of triangulating the signals. Due to the multitude of sensors 20 and their respective signals, the task of the central processor 28 is enormous. Also, because triangulation is accomplished by relating each sensor's signal to the signal of other sensors, each sensor must be precisely placed to insure accuracy. This increases the amount of time necessary to install the system. Furthermore, the complexity of the wiring 24, as well as the sheer weight of the wiring, is also substantial.

Figure 3:
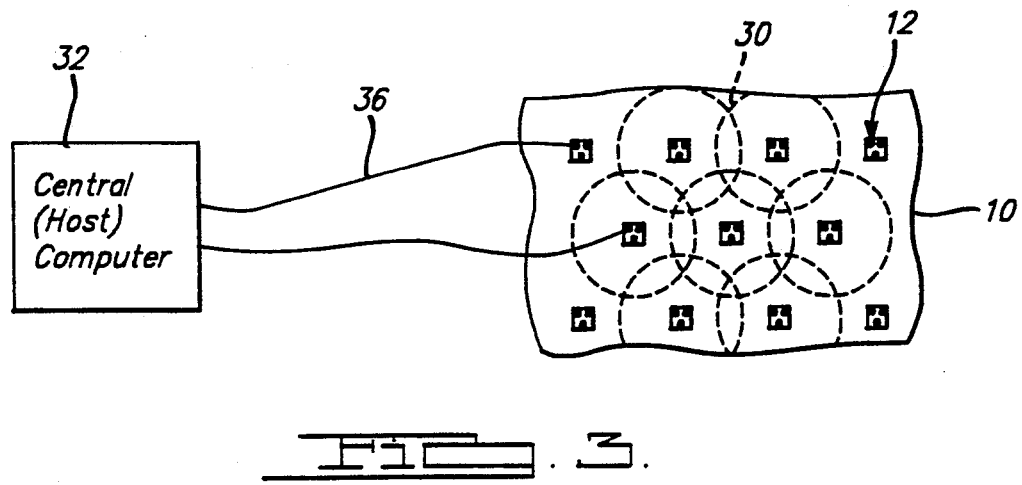
FIG. 3 is a diagram depicting a plurality of sensor patches of the present invention attached to a structure to be monitored.

In contrast, as shown in FIG. 3, the preferred embodiment of the present invention is markedly simpler to utilize. More specifically, in order to monitor the same surface area, in this example the interior skin of an airplane wing 10, the smart sensor patches 12 must be deployed such that any fatigue point that occurs lies within the coverage circle 30 of at least one sensor patch. This feature greatly reduces the number of smart sensor patches 12 required to cover a given surface 10 over the prior art. Each smart sensor patch 12 contains a local processor which accomplishes the task of triangulating the location of a fatigue point in relation to that smart sensor patch 12. The location of a fatigue point, as determined by each of the local processors can then be fed into a central, or host, computer 32 for compiling the location information and providing data for the operator. In the preferred embodiment, each smart sensor patch 12 is electronically linked to the central computer 32 via a serial bus 36.

Figure 4:
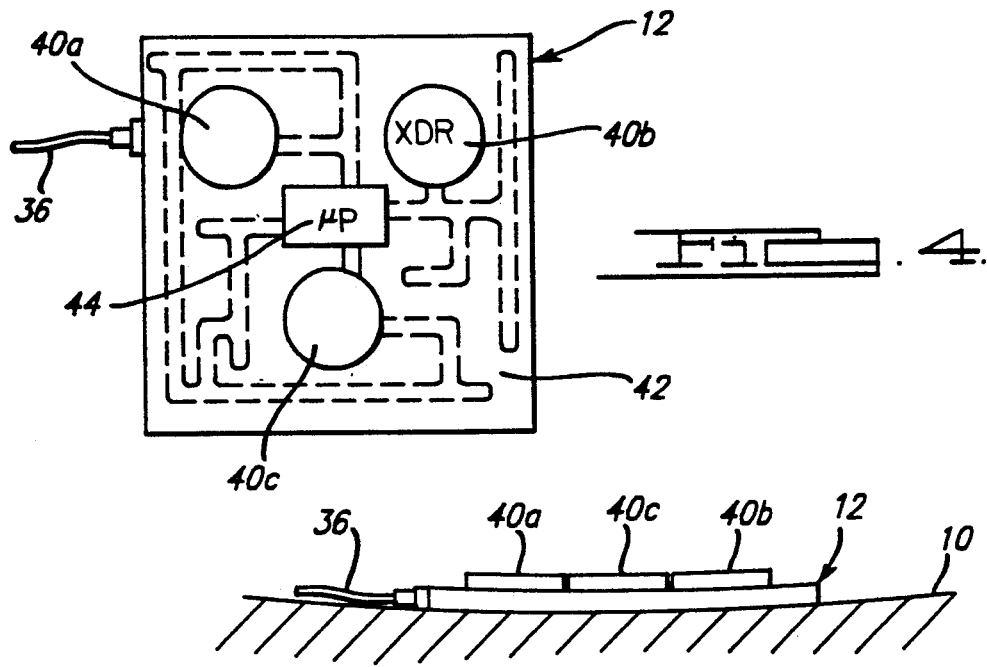
FIG. 4 is a plan view of an individual sensor patch.
Figure 5:
FIG. 5 is a side elevation of a sensor patch.

FIG. 4 is a detailed diagram of an individual smart sensor patch viewed in plan, while FIG. 5 is a diagram of the smart sensor patch 12 viewed in elevation. Each smart sensor patch 12 includes three triangularly adjacent acoustic sensors 40a–c mounted within a flexible circuit array 42. These acoustic sensors are preferably piezoelectric transducers. Also within the flexible circuit array 42 is a local processor 44. The local processor 44 conditions the signals generated by the acoustic sensors 40a-c and determines the locating of the fatigue point from those signals. The smart sensor patch 12 is affixed to the structure skin 10 using an adhesive. The adhesive allows the patch to be mounted quickly as well as allowing the flexible patch to conform to the surface of the skin 10. Ideally, the smart sensor patch is approximately 3"×3" so as to allow for easy placement on the structure as well as providing sufficient triangulation resolution by the acoustic sensors. This will be discussed in more detail later.

Figure 7:
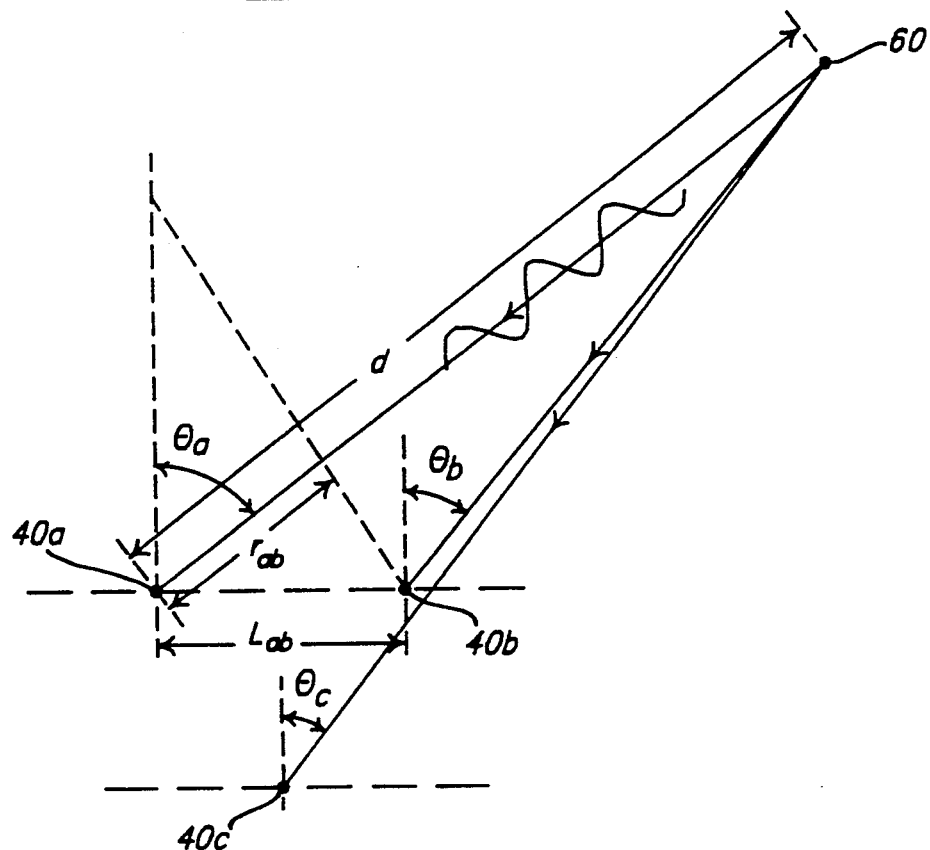
FIG. 7 is a diagram depicting the manner in which an incoming acoustic wave is sensed by the acoustic sensors of the sensor patch.

FIG. 6 is a functional block diagram showing the operation of the local processor 44. Each of the three triangularly adjacent acoustic sensors 40a-c of the smart sensor patch 12 are electronically coupled to the smart sensor's local processor 44 via the flexible circuit array 42. As is shown in FIG. 6, the signal generated by each of the acoustic sensors 40a-c are fed into a pre-amp conditioning circuit 50, then digitized by an A/D converter 52, converted from real into imaginary coordinates by the I/Q chip 53, and subsequently transformed into complex frequency domain Fourier coefficients by a fast Fourier transform, or FFT, circuitry 54. As can be seen in FIG. 6, a thresholding circuit 56 triggers the digital sampling of the acoustic signals by the A/D converters 52. It should be noted that the pre-computational sampling and conditioning of the signal, as performed by the pre-amp 50, A/D converter 52, I/Q chip 53, FFT circuit 54 and thresholding circuit 56 are well known to those skilled in the art. As such, a variety of such circuitry could be employed to accomplish the pre-computational sampling and conditioning of the acoustic signals. The processed and conditioned signals from the acoustic sensors 40 are then fed into a digital signal processor 58. Because the signals are conditioned using Fourier transforms, the digital signal processor 58 performs the task of triangulation in frequency, rather than time, domain. Utilizing the signals and the phase difference between the signals, the relative angle and relative distance of the fatigue point from the smart sensor patch are determined. This process of triangulation, as accomplished by the computational array 58, is best illustrated in FIG. 7. The triangulated location of the fatigue point is transmitted to the central computer via the serial I/0 interface 59.

When a fatigue point occurs in the structure, generally indicated as point 60 in the drawing, an acoustic wave is generated. As the acoustic wave front travels through the structure, it will be sensed by one or more of the smart sensor patches. More particularly, FIG. 7 depicts an incoming acoustic wave front as it approaches one of the smart sensor patches. It should be appreciated that the acoustic wave front would emanate circularly from the fatigue point 60, and would be sensed by at least one, and likely more than one, of the smart sensor patches. As the acoustic wave front arrives at a smart sensor patch, it is sensed, or detected, by each of the acoustic sensors 40a-c of the smart sensor patch. The acoustic wave front has an angle of arrival in relation to each acoustic sensor of theta (Θ).

Given that the distance between any of the acoustic sensors 40a-c is known, in this case indicated as L, the angle of arrival can be computed as follows:

$$\sin\theta \approx \frac{r}{L}$$

As indicted in FIG. 7, the angle of arrival in relation to each of the three acoustic sensors 40a-c thus needs to be calculated in order to triangulate the position of the fatigue point 60 in relation to the smart sensor patch.

In this embodiment, the process of triangulation is accomplished in the frequency domain. When designating the acoustic sensor a and b, from left to right, the phase difference between acoustic channel a and acoustic channel b, $\Phi_{ab}$ can be found as follows; Let $X_{na}$ be the $n^{th}$ sample of the FFT output for channel a and $X_{nb}$ be the $n^{th}$ sample or channel b. As such:

$$X_{na} = A_1 e^{i(\omega n + \phi a)} = a + ib$$

$$X_{na} = A_2 e^{i(\omega n + \phi b)} = c + id$$

$$\begin{aligned}X_{na}^* \times X_{nb} &= A_1 e^{-i(\omega n + \phi a)} \times A_2 e^{i(\omega n + \phi b)}\\ &= A_1 A_2 e^{i(\phi b - \phi a)}\\ &= (ac + bd) + i(ad - bc)\end{aligned}$$

Thus, the phase difference between channels a and b is:

$$\phi_{ab} = \phi_b - \phi_a$$

$$\phi_{ab} = \tan^{-1}\left[\frac{(ad - bc)}{(ac + bd)}\right]$$

In a similar manner, the phase difference between all of the channels can be computed.

The angle of arrival of the acoustic wave at the first sensor 40 can be calculated in the following manner:

$$\sin\theta \approx \frac{r_{ab}}{L_{ab}}$$

where $r_{ab}$ is the difference between two wavefronts and $L_{ab}$ is the distance between acoustic sensors a and b.

$$t_{ab} = \frac{r_{ab}}{v}$$

Where $t_{ab}$ is the travel time between sensors a and b, and $v$ is the acoustic velocity.

$$v = f_0 \lambda_0; \frac{r_{ab}}{\lambda} = \frac{\phi_{ab}}{2\pi}$$

by substituting:

$$t_{ab} = \frac{\phi_{ab}}{2\pi f_0}$$

$$\phi_{ab} = 2\pi f_0 t_{ab} = \frac{2\pi f_0 L_{ab}}{v} \sin\theta_a$$

$$\sin\theta_a = \frac{\phi_{ab} v}{2\pi f_0 L_{ab}} = \frac{\phi_{ab} \lambda_0 f_0}{2\pi f_0 L_{ab}} = \frac{\phi_{ab} \lambda_0}{2\pi L_{ab}}$$

It should be noted that the quantity $\lambda_o$, and hence $f_o$ and $v$, belong to any detected ringing frequency in the spectrum. For example, if the skin were composed of a metallic compound such as iron or aluminum, the acoustic velocity ($v$) would be approximately equal to 15,000 feet per second. Once the angle of arrival ($\Theta$) of the acoustic wave at each of the acoustic sensors 40 is calculated, it is a matter of simple geometry to determine the location of the fatigue point 60 in relation to the smart sensor patch. Specifically, $$d = \sqrt{x^2 + y^2}$$

where $$x = \frac{L}{\left[1 - \frac{\tan\theta_b}{\tan\theta_a}\right]} ; y = \frac{x}{\tan\theta_a}$$

It should be appreciated that in applications involving a multitude of smart sensor patches, as would be common when monitoring a structure such as an airplane skin or a bridge, the fact that the present invention provides for localized triangulation at each smart sensor patch greatly reduces the complexity of the computational task in determining the location of a fatigue point.

Referring once again, in general, to FIGS. 3–6, the size of the smart sensor patch and the degree of resolution accuracy can be tailored to fit most desired applications. For example, in the preferred embodiment, it is desirous to have a smart sensor patch of approximately 3"×3". Assuming the structure being monitored is a metallic compound, the acoustic velocity of a fatigue-generated acoustic wave is approximately equal to 15,000 feet per second. When assuming a maximum fatigue point generated acoustic frequency of 1 MHz, the wavelength, $\lambda$ is found to be:

$$\lambda = v/f = 0.44 \text{ cm}.$$

In order to provide for proper phase detection, the spacing between any two acoustic sensors should be M $\lambda/2$ where M is an integer and $\lambda$ is the maximum acoustic wavelength. If $M \leq 30$, then M $\lambda/2 = 6.60$ cm $< 3"$. Furthermore, assuming the distance resolution desired is 10 mm, then:

$$\lambda = 0.44 \text{ cm}$$

$$L = M \lambda/2$$

The area of coverage for the smart sensor patch is assumed to be 1 foot, or 29.4 cm. Given this, the time resolution needed for sampling the phase arrival at each acoustic sensor is:

$$t_s = \frac{t_1}{r/\alpha}$$

$$t_e = \frac{L}{v} = \frac{M\lambda/2}{v} \approx 15 \ \mu s$$

Where $t_l$ is the time from a to b, $\alpha$ is the space resolution and r is the radius of coverage for the smart sensor patch.

$$t_s = \frac{15(10)^{-6}}{29.4/1.0} = 0.05 \ \mu s$$

-continued $$f_s = \frac{1}{t_s} = 2 \text{ MHz} = \text{sampling rate}$$

Thus, as described in the preferred embodiment, smart sensor patches of dimensions 3"×3" are deployed across the surface of the structure, each smart sensor patch having a coverage radius of 1 foot. Furthermore, the space between adjacent acoustic sensors on the smart sensor patch is approximately 6.6 cm, and the sampling frequency for each acoustic sensor is 2 MHz. Thus, it can be appreciated that the spacing between adjacent acoustic sensors as well as the sampling frequency at each acoustic sensor can be tailored to fit the desired application. Furthermore, the preceding description of the preferred embodiment was provided as an illustration of one manner in which to practice the invention, and design-specific modifications could be performed using ordinary skill i the art without departing from the spirit and scope of the invention.

What is claimed is:

1. A system for locating a fatigue point on a structure wherein the emergence of the fatigue point propagates an acoustic wave through the structure, the system comprising:
   at least one sensor patch, having a base layer, attached to the structure;
   three triangularly adjacent sensor means, attached to said base layer of said sensor patch, for generating signals in response to receiving the incoming propagated acoustic wave;
   processing means, located on said sensor patch and coupled to each of said sensor means, for determining the location of the fatigue point on the structure as a function of said generated signals from said sensor means;
   a plurality of said sensor patches and a plurality of processing means, each sensor patch having a processing means associated therewith; and
   a central processor means for collecting said determined fatigue point locations from each of said processing means.

2. The system of claim 1 wherein said processing means determines the location of the fatigue point by comparing the phase difference between said signals generated by said sensor means.

3. The system of claim 1 wherein said sensor means are equidistantly triangularly adjacent.

4. The system of claim 1 wherein said base layer of said sensor patch is flexible and resilient.

5. The system of claim 1 wherein said sensor means are piezoelectric transducers.

6. A system for locating a fatigue point on a structure wherein an acoustic signal is propagated through the structure when the fatigue point emerges, the system comprising:
   a plurality of sensor patches attached to the structure, each sensor patch having a base layer and three triangularly adjacent acoustic sensors attached to said base layer, wherein each acoustic sensor generates a signal in response to receiving the propagated acoustic signal;
   a plurality of processing means, one said processing means located on each of said sensor patches, each said processing means being coupled to said acoustic sensors on said sensor patch, for determining the location of the fatigue point in relation to the position of said sensor patch on the structure; and a central processing means for collecting said determined relative fatigue point locations from each of said processing means.

7. A system of claim 6 wherein each of said processing means determines the relative location of the fatigue point in relation to the position of said sensor patch by determining the phase difference between said generated signals from said acoustic sensors on said sensor patch.

8. A system of claim 6 wherein said base layer of said sensor patch is flexible and resilient.

9. A system of claim 6 wherein said acoustic sensors are comprised of piezoelectric transducers.

10. A system of claim 6 wherein said acoustic sensors are equidistantly triangularly adjacent.

11. A method for locating a fatigue point on a structure, the method comprising:

attaching three triangularly adjacent acoustic sensor to a sensor patch;

attaching a processor to said sensor patch;

attaching said sensor patch to the surfaces of the structure;

receiving an acoustic signal at said acoustic sensors, said acoustic signal being propagated by the emergence of a fatigue point on the structure;

generating an electric signal from each of said acoustic sensors in response to said receiving of said acoustic signal;

coupling said generated signals to said processor;

using said processor to compute the phase difference between said generated signals from each of said acoustic sensors;

attaching a plurality of said sensor patches to the structure;

determining the location of the fatigue point in relation to the location of each of said sensor patches;

coupling a central computer means to each of said processors on said sensor patches;

determining the location of the fatigue point as a function of said determined relative fatigue point locations transmitted from said processors to said central computer means; and determining the location of the fatigue point as a function of said computed phase difference.

12. A method of claim 11 wherein said acoustic sensors are equidistantly triangularly adjacent.

13. A method of claim 11 wherein said sensor patch is attached to the structure by an adhesive.

14. A method of claim 11 wherein said sensor patch has a flexible and resilient base layer which is attached to the structure and upon which is attached said acoustic sensors.

15. A method of claim 11 wherein said acoustic sensors are piezoelectric transducers.

* * * * *